(12) United States Patent
Hassan

(10) Patent No.: US 7,303,765 B2
(45) Date of Patent: Dec. 4, 2007

(54) ULTRAFINE-L-CARNITINE, METHODS OF PREPARING THE SAME, COMPOSITIONS CONTAINING THE SAME, AND METHODS OF USING THE SAME

(75) Inventor: Ken Hassan, Malvern, PA (US)

(73) Assignee: Sigma-Tau HealthScience S.p.A., Pomezia (IT)

( * ) Notice: Subject to any disclaimer, the term of this patent is extended or adjusted under 35 U.S.C. 154(b) by 237 days.

(21) Appl. No.: 11/041,272

(22) Filed: Jan. 25, 2005

(65) Prior Publication Data

US 2005/0124558 A1    Jun. 9, 2005

Related U.S. Application Data

(63) Continuation of application No. 10/073,978, filed on Feb. 14, 2002, now abandoned, which is a continuation of application No. 09/653,861, filed on Sep. 1, 2002, now abandoned.

(60) Provisional application No. 60/152,240, filed on Sep. 3, 1999, provisional application No. 60/158,245, filed on Oct. 8, 1999.

(51) Int. Cl.
*A61K 9/14*      (2006.01)
*A61K 9/20*      (2006.01)
*A61K 9/26*      (2006.01)
*A61K 9/50*      (2006.01)
*A61K 9/54*      (2006.01)

(52) U.S. Cl. ............... 424/489; 424/451; 424/458; 424/464; 424/469; 424/499

(58) Field of Classification Search .............. None
See application file for complete search history.

(56) References Cited

U.S. PATENT DOCUMENTS

| 5,057,597 | A | * | 10/1991 | Koskan | 528/328 |
| 5,753,234 | A | * | 5/1998 | Lee et al. | 424/204.1 |
| 6,090,849 | A | * | 7/2000 | Teeter et al. | 514/556 |
| 6,149,939 | A | * | 11/2000 | Strumor et al. | 424/464 |
| 6,242,487 | B1 | * | 6/2001 | Blum et al. | 514/561 |
| 6,476,010 | B2 | * | 11/2002 | Koo et al. | 514/168 |
| 6,485,741 | B2 | * | 11/2002 | Hassen | 424/451 |
| 6,488,961 | B1 | * | 12/2002 | Robinson et al. | 424/466 |

* cited by examiner

*Primary Examiner*—S. Tran
(74) *Attorney, Agent, or Firm*—Lucas & Mercanti, LLP

(57) ABSTRACT

L-carnitine which has a particle size such that it substantially passes through a 100 USBS mesh sieve exhibits an increased bioavailability, a decreased hygroscopicity, and may be conveniently formulated with oil-based materials.

11 Claims, No Drawings

US 7,303,765 B2

ULTRAFINE-L-CARNITINE, METHODS OF PREPARING THE SAME, COMPOSITIONS CONTAINING THE SAME, AND METHODS OF USING THE SAME

This patent application is a continuation of U.S. Ser. No. 10/073,978, filed on Feb. 14, 2002, now abandoned, which in turn is a continuation of U.S. Ser. No. 09/653,861, filed on Sep. 1, 2000, now abandoned, and which in turn claims the benefit of U.S. Provisional Application No. 60/152,240 filed on Sep. 3, 1999, and U.S. Provisional Application No. 60/158,245 filed on Oct. 8, 1999.

BACKGROUND OF THE INVENTION

1. Field of the Invention

The present invention relates to an ultra-fine L-carnitine and salts thereof. In particular, the present invention relates to L-carnitine and salts thereof which exist in the form of ultra-fine particles. The present ultra-fine L-carnitine is capable of being uniformly blended with fine particles of other raw materials, while maintaining its own discrete shape. The overall fineness of the present ultra-fine L-carnitine makes it ideal for blending with oil-based raw materials with which conventional bulk carnitine is not entirely miscible. The overall fineness of the present ultra-fine L-carnitine also facilitates the ready absorption in the gut due to the increased overall surface area of the fine material. The present invention also relates to methods for preparing such ultra-fine L-carnitine and salts thereof. The present invention further relates to compositions which comprise such ultra-fine L-carnitine and salts thereof. The present invention additionally relates to methods of using such ultra-fine L-carnitine and salts thereof.

2. Description of the Background

L-carnitine is known to have many uses. In particular, the oral administration of L-carnitine has been shown to be an effective therapy for cardiovascular diseases. L-carnitine and its salts are also known to be useful as dietary supplements, in particular for the facilitation of the metabolism of lipids.

However, it is desired to increase the bioavailability of L-Carnitine and its well known salts. It is also desired to prepare compositions which contain L-carnitine and one or more other ingredients with which bulk L-carnitine is not miscible, e.g., oil-based raw materials. It is further desired to reduce the hygroscopicity of L-carnitine.

Thus, there remains a need for forms of L-carnitine and salts thereof which exhibit increased bioavailability upon oral administration. There also remains a need for forms of L-carnitine and salts thereof which can be easily formulated with other ingredients with which bulk L-carnitine is not miscible, e.g., oil-based raw materials. There also remains a need for forms of L-carnitine and salts thereof which exhibit a decreased hygroscopicity.

SUMMARY OF THE INVENTION

Accordingly, it is one object of the present invention to provide novel forms of L-carnitine and salts thereof which exhibit an increased bioavailability upon oral administration.

It is another object of the present invention to provide novel forms of L-carnitine and salts thereof which can be easily formulated with other ingredients with which bulk L-carnitine is not miscible, e.g., oil-based raw materials.

It is another object of the present invention to provide novel forms of L-carnitine and salts thereof which exhibit a reduced hygroscopicity.

It is another object of the present invention to provide novel methods of preparing such L-carnitine.

It is another object of the present invention to provide novel compositions which contain such L-carnitine.

It is another object of the present invention to provide novel methods of using such L-carnitine.

These and other objects, which will become apparent during the following detailed description, have been achieved by the inventors' discovery that L-carnitine and salts thereof which exist in the form of ultra-fine particles exhibit a high bioavailability upon oral administration. The inventors have also discovered that such L-carnitine may be conveniently formulated with oil-based raw materials. The inventors have also discovered that such L-carnitine exhibits a reduced hygroscopicity.

DETAILED DESCRIPTION OF THE PREFERRED EMBODIMENTS

Thus, in a first embodiment, the present invention provides ultra-fine L-carnitine and salts thereof. In the context of the present invention, the term L-carnitine and salts thereof includes not only L-carnitine itself, but also salts of L-carnitine, alkanoyl L-carnitines, and salts of alkanoyl L-carnitine. Suitable salts of L-carnitine include L-carnitine chloride, L-carnitine bromide, L-carnitine orotate, L-carnitine acid aspartate, L-carnitine acid phosphate, L-carnitine fumarate, L-carnitine lactate, L-carnitine maleate, L-carnitine acid maleate, L-carnitine acid oxalate, L-carnitine acid sulfate, L-carnitine glucose phosphate, L-carnitine tartrate, L-carnitine acid tartrate, L-carnitine iodate, L-carnitine aspartate, L-carnitine citrate, L-carnitine acid citrate, L-carnitine acid fumarate, L-carnitine glycerophosphate, L-carnitine mucate, L-carnitine orotate, L-carnitine oxalate, L-carnitine sulfate, L-carnitine trichloroacetate, L-carnitine trifluoroacetate, L-carnitine methanesulfonate, L-carnitine pamoate, and L-carnitine acid pamoate.

Suitable alkanoyl L-carnitines include $C_{2-8}$ alkanoyl L-carnitines, particularly acetyl, butyryl, isobutyryl, valeryl, isovaleryl and more particularly propionyl L-carnitine Suitable salts of alkanoyl L-carnitines include $C_{2-8}$ alkanoyl L-carnitine chloride, $C_{2-8}$ alkanoyl L-carnitine bromide, $C_{2-8}$ alkanoyl L-carnitine orotate, $C_{2-8}$ alkanoyl L-carnitine acid aspartate, $C_{2-8}$ alkanoyl L-carnitine acid phosphate, $C_{2-8}$ alkanoyl L-carnitine fumarate, $C_{2-8}$ alkanoyl L-carnitine lactate, $C_{2-8}$ alkanoyl L-carnitine maleate, $C_{2-8}$ alkanoyl L-carnitine acid maleate, $C_{2-8}$ alkanoyl L-carnitine acid oxalate, $C_{2-8}$ alkanoyl L-carnitine acid sulfate, $C_{2-8}$ alkanoyl L-carnitine glucose phosphate, $C_{2-8}$ alkanoyl L-carnitine tartrate, $C_{2-8}$ alkanoyl L-carnitine acid tartrate, $C_{2-8}$ alkanoyl L-carnitine iodate, $C_{2-8}$ alkanoyl L-carnitine aspartate, $C_{2-8}$ alkanoyl L-carnitine citrate, $C_{2-8}$ alkanoyl L-carnitine acid citrate, $C_{2-8}$ alkanoyl L-carnitine acid fumarate, $C_{2-8}$ alkanoyl L-carnitine glycerophosphate, $C_{2-8}$ alkanoyl L-carnitine mucate, $C_{2-8}$ alkanoyl L-carnitine orotate, $C_{2-8}$ alkanoyl L-carnitine oxalate, $C_{2-8}$ alkanoyl L-carnitine sulfate, $C_{2-8}$ alkanoyl L-carnitine trichloroacetate, $C_{2-8}$ alkanoyl L-carnitine trifluoroacetate, $C_{2-8}$ alkanoyl L-carnitine methanesulfonate, $C_{2-8}$ alkanoyl L-carnitine pamoate, and $C_{2-8}$ alkanoyl L-carnitine acid pamoate.

Thus, the present invention provides ultra-fine particles of L-carnitine, as well as ultra-fine particles of a salt of L-carnitine. The present invention also provides mixtures of ultra-fine particles of L-carnitine and ultra-fine particles of one or more salts of L-carnitine, as well as mixtures of ultra-fine particles of two or more salts of L-carnitine.

The ultra-fine L-carnitine and salts thereof of the present invention has a particle sufficiently small that substantially all of it passes through a 100 United State Bureau of Standards (USBS) mesh screen. In a preferred embodiment, the ultra-fine L-carnitine and salts thereof of the present invention has a particle sufficiently small that substantially all of it passes through a 150 USBS mesh screen. In a particularly preferred embodiment, the ultra-fine L-carnitine and salts thereof of the present invention has a particle sufficiently small that substantially all of it passes through a 200 USBS mesh screen.

The ultra-fine L-carnitine and salts thereof of the present invention may be prepared by reducing the size of conventional L-carnitine and salts thereof and selecting the appropriately sized particles by sieving. Currently, L-carnitine and salts thereof are conveniently prepared by the methods described in U.S. Pat. Nos. 4,254,053; 4,602,039; and 5,412,113 and European Patent Application EP-A-0150688, which are incorporated herein by reference. Such procedures typically yield L-carnitine having a size of such that greater than 10% by weight of the L-carnitine is retained by a 50 mesh sieve and more than 40% by weight is retained by a 100 mesh sieve. The present ultra-fine L-carnitine may be produced by subjecting such L-carnitine to size reduction. The size reduction may be carried out by any suitable technique, such as grinding, milling, etc. Methods of size reduction are well known and are described in Kirk-Othmer, *Encyclopedia of Chemical Technology*, $4^{th}$ Ed., Wiley, New York, vol. 22, pp. 279-296, 1999, which is incorporated herein by reference.

After the conventionally prepared L-carnitine has been subjected to size reduction, the ultra-fine l-carnitine of the present invention may be selected by subjecting the size-reduced L-carnitine to sieving. Sieving is a well known technique for selecting materials of a particular size and is described in Kirk-Othmer, *Encyclopedia of Chemical Technology*, $4^{th}$ Ed., Wiley, New York, vol. 22, pp. 256-278, 1999, which is incorporated herein by reference. The ultra-fine L-carnitine of the present invention is obtained by selecting that material which passes through a 100 USBS mesh sieve, preferably a 150 USBS mesh sieve, more preferably a 200 mesh USBS mesh sieve.

In another embodiment, the present invention provides compositions which contain the ultra-fine L-carnitine and a pharmaceutically acceptable excipient or carrier. Suitable pharmaceutically acceptable excipients or carriers are described in Remington's Pharmaceutical Sciences Handbook, Mack Publishing, which is incorporated herein by reference.

In a preferred embodiment, the pharmaceutically acceptable excipient or carrier is an oil-based material, such as synthetic or natural oil based vitamins including, but not limited to vitamin E, oils extracted from any seed or vegetable such as, but not limited to soy, olive, palm, or corn oil, and any nutritive substance that maybe previously dissolved suspended or mixed in one or more of such oils.

The present compositions will suitably contain the ultra-fine L-carnitine in an amount of 10 to 99% by weight, preferably 25 to 95% by weight, more preferably 50 to 90% by weight, based on the total weight of the composition. The present composition may take the form of soft gelatin capsules, powders, pills, tablets, etc. In a preferred embodiment, the present composition is in the form of a gelatin capsule, pre-mix, sachet or reconstitutable sports drink mix.

The present composition may further comprise any of the additional active ingredients which L-carnitine or salts thereof are known to be combined with, e.g., hydroxycitric acid, Co-enzyme Q10, chromium picolinate, gamma linolenic acid, resveratrol, omega 3 acids, antioxidants, vitamins, etc.

In another embodiment, the present invention provides methods of treatment, therapy, and prevention involving orally administering to a subject in need of such treatment, therapy, or prevention, an effective amount of the ultra-fine L-carnitine or salt thereof of the present invention. Methods of treatment, therapy, and/or prevention in which the ultra-fine L-carnitine of the present invention may be used are described in U.S. Pat. Nos. 4,474,812 and 5,861,434, which are incorporated herein by reference.

The compound of the invention will have a minimum active principle of 57%, and still be capable of extended shelf life in combination formulations contained within soft gelatin capsules, pre-mixes, sachets and reconstitutable sports drink mixes. A transformer (a person or entity which will transform the present ultrafine L-carnitine into a finished product) will succeed in planned remote geographic markets for dry products that may be shipped and warehoused economically, then reconstituted locally, realizing a cost savings and increased opportunity for customers.

There are also peripheral benefits since the present ultra-fine L-carnitine and salts thereof are probably the best L-Carnitine source for combination formulations such as L-Carnitine and Co-enzyme Q10, due the similarity of particle sizes.

Ultra-fine L-carnitine fumarate and therefore the compound of the present invention has been shown to demonstrate an increased bioavailability through the mitochondrial pathway. This effect is substantiated with studies that show human plasma levels to equal those of conventionally sized L-carnitine tartrate for identical prior dosing. Transformers may therefore accomplish the target dosage using a reduced active bolus, an efficiency which translates to cost savings. In principle, consumers purchase nutritionals on a pure weight volume (W/V) basis. The marketer who adds more active weight is judged as having a higher quality product.

The compound of the invention may be certified "BSE Safe," since it contains no animal products and is based upon chemical synthesis. Avoidance of potential health risks and unnecessary consumption of unknown organisms, since tartrate is a bioferm. "International Food Marketing," GreenPeace and others have published articles on the future risk of BSE. The buying public has a heightened awareness to this risk.

The compound of the present invention requires no reworking (regranulation, conditioning) as tartrate does. Lowered production costs, labor, environmental exposure. If transformer is not reworking tartrate, they should, since tablets made with tartrate as is will not hold up well in gelatine capsules or on shelves.

The fine particle size (200 Mesh) and coating of hydrophilic and or hydrophobic silicas provides excellent mixing and content uniformity properties especially for formulations that use other finely particled ingredients such as chromium picolinate and Co-enzyme Q10, as well as extended shelf life due to its inherently low hygroscopicity. Tooling (punches) and presses theoretically run cooler, than with tartrate, due to increased lubricity offered by the silica, which will save expensive downtime thereby reducing costs.

The present ultra-fine L-carnitine is particularly useful as a dietary supplement to ensure a healthy and balanced diet. It is also useful as a cofactor for weight control and as a dietary supplement for sport nutrition, vegetarian nutrition, animal nutrition. It is also useful in veterinary nutrition.

Other features of the invention will become apparent in the course of the following descriptions of exemplary embodiments which are given for illustration of the invention and are not intended to be limiting thereof.

EXAMPLE

In the following examples, and throughout this specification, all parts and percentages are by weight, and all temperatures are in degrees Celsius, unless expressly stated to be otherwise. Where the solids content of a dispersion or solution is reported, it expresses the weight of solids based on the total weight of the dispersion or solution, respectively. Where a molecular weight is specified, it is the molecular weight range ascribed to the product by the commercial supplier, which is identified. Generally this is believed to be weight average molecular weight.

Example 1

L-carnitine fumarate is milled to an over all particle size so as to minimally pass a number 100 USBS Mesh screen. Particles utilized to evaluate the efficacy of the invention to date have actually been milled to pass 150-200 Mesh with outstanding results. Particles are then blended with a food grade hydrophilic and/or hydrophobic fumed or precipitated silica(s) of the type available from Degussa, Inc. that poses an overall surface area of 190-475 square meters per gram and a tapped density of 80-275 grams per liter.

Ultra-fine L-carnitine fumarate so prepared has the following analytical properties:

| | |
|---|---|
| Description: | white crystalline powder |
| Assay: | 58.0% ± 2% carnitine |
| | 41.5% ± 1% fumaric acid |
| Water content: | ≦1% (Karl Fischer) |
| Specific rotation: | $[\alpha]_D^{20} = 17.5° \pm 1°$ (1% in water) |
| pH: | 3.0 to 4.0 (1% in water) |
| Solubility: | 5 g/100 ml in water |
| Mesh size: | Passes 150 mesh conditioned with fumed food grade silica |
| Toxicity: | $LD_{50}$ (oral) > 8,000 mg/kg (rats) |

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

This application is based on U.S. Provisional Application 60/152,240 filed on Sep. 3, 1999, and U.S. Provisional Application 60/158,245 filed on Oct. 8, 1999, both of which are incorporated herein by reference in their entirety.

What is claimed as new and desired to be secured by Letters Patent of the United States is:

1. A composition, consisting of L-carnitine particles, having a particle size such that the particles substantially pass through a 100 USBS mesh sieve blended with a silica having an overall surface area of from 190 to 475 square meters per gram and a tapped density of from 80 to 275 grams per liter wherein L-carnitine is present in an amount of 10% to 99% by weight, based on the total weight of the composition.

2. The composition of claim 1, which is selected from the group consisting of L-carnitine, salts of L-carnitine, alkanoyl L-carnitines, and salts of alkanoyl L-carnitine.

3. The composition of claim 1, which is selected from the group consisting of L-carnitine chloride, L-carnitine bromide, L-carnitine orotate, L-carnitine acid aspartate, L-carnitine acid phosphate, L-carnitine fumarate, L-carnitine lactate, L-carnitine maleate, L-carnitine acid maleate, L-carnitine acid oxalate, L-carnitine acid sulfate, L-carnitine glucose phosphate, L-carnitine tartrate, L-carnitine acid tartrate, L-carnitine iodate, L-carnitine aspartate, L-carnitine citrate, L-carnitine acid citrate, L-carnitine acid fumarate, L-carnitine glycerophosphate, L-carnitine mucate, L-carnitine orotate, L-carnitine oxalate, L-carnitine sulfate, L-carnitine trichloroacetate, L-carnitine trifluoroacetate, L-carnitine methanesulfonate, L-carnitine pamoate, L-carnitine acid pamoate, $C_{2-8}$ alkanoyl L-carnitines, $C_{2-8}$ alkanoyl L-carnitine chloride, $C_{2-8}$ alkanoyl L-carnitine bromide, $C_{2-8}$ alkanoyl L-carnitine orotate, $C_{2-8}$ alkanoyl L-carnitine acid aspartate, $C_{2-8}$ alkanoyl L-carnitine acid phosphate, $C_{2-8}$ alkanoyl L-carnitine fumarate, $C_{2-8}$ alkanoyl L-carnitine lactate, $C_{2-8}$ alkanoyl L-carnitine maleate, $C_{2-8}$ alkanoyl L-carnitine acid maleate, $C_{2-8}$ alkanoyl L-carnitine acid oxalate, $C_{2-8}$ alkanoyl L-carnitine acid sulfate, $C_{2-8}$ alkanoyl L-carnitine glucose phosphate, $C_{2-8}$ alkanoyl L-carnitine tartrate, $C_{2-8}$ alkanoyl L-carnitine acid tartrate, $C_{2-8}$ alkanoyl L-carnitine iodate, $C_{2-8}$ alkanoyl L-carnitine aspartate, $C_{2-8}$ alkanoyl L-carnitine citrate, $C_{2-8}$ alkanoyl L-carnitine acid citrate, $C_{2-8}$ alkanoyl L-carnitine acid fumarate, $C_{2-8}$ alkanoyl L-carnitine glycerophosphate, $C_{2-8}$ alkanoyl L-carnitine mucate, $C_{2-8}$ alkanoyl L-carnitine orotate, $C_{2-8}$ alkanoyl L-carnitine oxalate, $C_{2-8}$ alkanoyl L-carnitine sulfate, $C_{2-8}$ alkanoyl L-carnitine trichloroacetate, $C_{2-8}$ alkanoyl L-carnitine trifluoroacetate, $C_{2-8}$ alkanoyl L-carnitine methanesulfonate, $C_{2-8}$ alkanoyl L-carnitine pamoate, and $C_{2-8}$ alkanoyl L-carnitine acid pamoate.

4. A method of preparing a composition, consisting of (1) subjecting L-carnitine having a particle size such that it does not pass through a 100 USBS mesh sieve to size reduction, to obtain size-reduced L-carnitine; (2) subjecting said size-reduced L-carnitine to sieving through a 100 USBS mesh sieve (3) selecting the portion which passes through said 100 USBS mesh sieve and blending said portion with a silica having an overall surface area of from 190 to 475 square meters per gram and a tapped density of from 80 to 275 grams per liter wherein L-carnitine is present in amount of 10% to 99% by weight, based on the total weight of the composition.

5. The method of claim 4, wherein said L-carnitine is selected from the group consisting of L-carnitine, salts of L-carnitine, alkanoyl L-carnitines, and salts of alkanoyl L-carnitine.

6. The method of claim 4, wherein said L-carnitine is selected from the group consisting of L-carnitine chloride, L-carnitine bromide, L-carnitine orotate, L-carnitine acid aspartate, L-carnitine acid phosphate, L-carnitine fumarate, L-carnitine lactate, L-carnitine maleate, L-carnitine acid maleate, L-carnitine acid oxalate, L-carnitine acid sulfate, L-carnitine glucose phosphate, L-carnitine tartrate, L-carnitine acid tartrate, L-carnitine iodate, L-carnitine aspartate, L-carnitine citrate, L-carnitine acid citrate, L-carnitine acid fumarate, L-carnitine glycerophosphate, L-carnitine mucate, L-carnitine orotate, L-carnitine oxalate, L-carnitine sulfate, L-carnitine trichloroacetate, L-carnitine trifluoroacetate, L-carnitine methanesulfonate, L-carnitine pamoate, L-carnitine acid pamoate, $C_{2-8}$ alkanoyl L-carnitines, $C_{2-8}$ alkanoyl L-carnitine chloride, $C_{2-8}$ alkanoyl L-carnitine bromide, $C_{2-8}$ alkanoyl L-carnitine orotate, $C_{2-8}$ alkanoyl L-carnitine acid aspartate, $C_{2-8}$ alkanoyl L-carnitine acid phosphate, $C_{2-8}$ alkanoyl L-carnitine fumarate, $C_{2-8}$ alkanoyl L-carnitine lactate, $C_{2-8}$ alkanoyl L-carnitine maleate, $C_{2-8}$ alkanoyl L-carnitine acid maleate, $C_{2-8}$ alkanoyl L-carnitine acid oxalate, $C_{2-8}$ alkanoyl L-carnitine acid sulfate, $C_{2-8}$ alkanoyl L-carnitine glucose phosphate, $C_{2-8}$ alkanoyl L-carnitine tartrate, $C_{2-8}$ alkanoyl L-carnitine acid tartrate, $C_{2-8}$ alkanoyl L-carnitine iodate, $C_{2-8}$ alkanoyl L-carnitine aspartate, $C_{2-8}$ alkanoyl L-carnitine citrate, $C_{2-8}$ alkanoyl L-carnitine acid citrate, $C_{2-8}$ alkanoyl L-carnitine acid fumarate, $C_{2-8}$ alkanoyl L-carnitine glycerophosphate, $C_{2-8}$ alkanoyl L-carnitine mucate, $C_{2-8}$ alkanoyl L-carnitine orotate, $C_{2-8}$ alkanoyl L-carnitine oxalate, $C_{2-8}$ alkanoyl L-carnitine sulfate, $C_{2-8}$ alkanoyl L-carnitine trichloroacetate, $C_{2-8}$ alkanoyl L-carnitine trifluoroacetate, $C_{2-8}$ alkanoyl L-carnitine methanesulfonate, $C_{2-8}$ alkanoyl L-carnitine pamoate, and $C_{2-8}$ alkanoyl L-carnitine acid pamoate.

7. The composition of claim 1, which is suitable for oral ingestion.

8. The composition of claim 1, wherein the L-carnitine particles have a particle size such that they substantially pass through a 150 USBS mesh sieve.

9. The composition of claim 1, wherein the L-carnitine particles have a particle size such that they substantially pass through a 200 USBS mesh sieve.

10. The L-carnitine containing composition of claim 1 wherein the L-carnitine is L-carnitine fumarate.

11. A composition, consisting of L-carnitine particles, having a particle size such that the particles substantially pass through a 100 USBS mesh sieve blended with a silica having an overall surface area of from 190 to 475 square meters per gram and a tapped density of from 80 to 275 grams per liter, and a member of the group consisting of hydroxycitric acid, Co-enzyme Q10, chromium picolinate, gamma linolenic acid, resveratrol, omega 3 acids, antioxidants, and vitamins, wherein L-carnitine is present in an amount of 10% to 99% by weight, based on the total weight of the composition.

* * * * *

UNITED STATES PATENT AND TRADEMARK OFFICE
CERTIFICATE OF CORRECTION

| | | |
|---|---|---|
| PATENT NO. | : 7,303,765 B2 | Page 1 of 1 |
| APPLICATION NO. | : 11/041272 | |
| DATED | : December 4, 2007 | |
| INVENTOR(S) | : Ken Hassen | |

It is certified that error appears in the above-identified patent and that said Letters Patent is hereby corrected as shown below:

On title page

In Box 75, "Hassan" should read --Hassen--

In Box 63, "2002" should read --2000--

Signed and Sealed this

Third Day of June, 2008

JON W. DUDAS
*Director of the United States Patent and Trademark Office*